Cover page — omitted.

1-((2-FLUOROPHENYL)(4-FLUOROPHENYL)-PHENYLMETHYL)-1H-IMIDAZOLE USEFUL AS ANTIFUNGAL AGENT

This is a continuation of application Ser. No. 07/257,095, filed Oct. 13, 1988, now abandoned.

The present invention relates to 1-[(2-fluorophenyl)(4-fluorophenyl)phenylmethyl]-1H-imidazole (I) and its suitable pharmaceutically acceptable salts, a process for its production, and a method of treating fungal infections which comprises administering such compound or its salts.

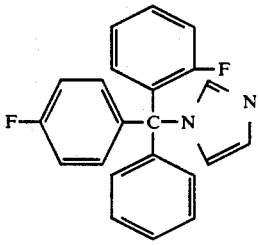

I

It was disclosed more than twenty years ago (in published patent applications ZA 68/5392 and ZA 69/0039) that some ring-substituted N-tritylimidazoles (II) are active against plant-pathogenic and animal pathogenic fungi. Since then many of such compounds have been prepared and their antifungal activities have been tested. A review article of 1972 (K. H. Büchel, W. Draber, E. Regel and M. Plemple, *Arzneim. Forsch.* 1972, 22, 1260-1272) collects physical and pharmacological data of 112 of such compounds.

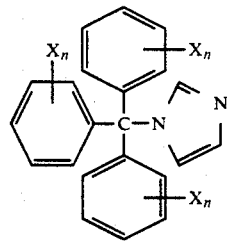

II

Despite the usefulness of the already known commercial antifungal compounds, the research in this field is still very intensive. New compounds (miconazole, econazole ...), and notably bifonazole (1-[(4-biphenyl)-phenylmethyl]-1H-imidazole, are being introduced in the market, in order to fight against fungal infections, particularly those caused by species that have become resistant to old compounds. Such infections represent a real problem, especially in big towns and hospitals.

Although all difluoro-substituted N-tritylimidazoles (both those substituted in one phenyl ring, and those substituted in two different phenyl rings) were included in the general formula of the first patents (ZA 68/5392 and its equivalents), none of them was actually prepared and/or tested on that occasion. According to the cited review article in *Arzneim. Forsch.*, none of the difluoro-substituted compounds was known as antifungal in 1972.

To the best of our knowledge, 1-[bis(4-fluorophenyl)-phenylmethyl]-1H-imidazole is the only N-tritylimidazole, difluoro-substituted in different phenyl rings, that has been described. This compound has been mentioned in a patent (EP 165.777), but for the prevention of estrogen-dependent diseases (especially breast cancer), which is a therapeutic indication unrelated to the one of the present invention.

Some dichloro or chlorofluoro N-tritylimidazoles, di-substituted in different phenyl rings, are already known, but-in the few cases tested-their antifungal activity is minor (cf. the cited article in *Arzneim. Forsch.*). An attempt of Quantitative Structure Activity Relationship study for mono-, di-and tri-substituted N-tritylimidazoles, has failed to reveal the structural factors responsible for the antifungal activity (cf. the same article). Therefore, it is unpredictable how active a particular di-substituted compound would be, if it is not prepared and tested. Other unpredictable characteristics, like absorption facility and/or low toxicity can also play an important role in the global therapeutical activity. Finally, a new compound can be surprisingly active to particular species of fungi, thus representing an advantage over other known compounds in some diseases.

Having in mind the state of the art relevant to substituted N-tritylimidazoles as antifungal agents, it is understandable that several selection inventions have been made in the past. Patents have been granted for some particular compounds, specially useful, even when there was a valid general claim comprising them. Thus, for instance, 1-[(2-chlorophenyl)(2'-chlorophenyl)-phenylmethyl]-1H-imidazole was patented per-se (U.S. Pat. No. 4,052,409), although such compound was already claimed—but not described—in ZA 68/5392.

We considered that the antifungal activity of difluoro N-tritylimidazoles (III), substituted in different phenyl rings, had not been investigated enough (none of them was known or tested; only a trifluoro-substituted compound was tested, showing no activity). Therefore, we have prepared and tested the following new compounds: 1-[(2-fluorophenyl)(3-fluorophenyl)phenylmethyl]-1H-imidazole (UR-4055), 1-[(2-fluorophenyl)(4-fluorophenyl)phenylmethyl]-1H-imidazole (UR-4056), 1-[bis(3-fluorophenyl)phenylmethyl]-1H-imidazole (UR-4057), 1-[(3-fluorophenyl)(4-fluorophenyl)phenylmethyl]-1H-imidazole (UR-4058), and 1-[bis(4-fluorophenyl)phenylmethyl]-1H-imidazole (UR-4059, mentioned in EP 165.777, but without giving identification data or preparation instructions). The examples of the present invention provide detailed processes for the preparation of these five compounds in good yields.

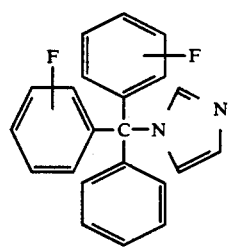

III

In our preliminary tests, all of these five compounds have shown antifungal activity. However, surprisingly, only one, compound 1-[(2-fluorophenyl)(4-fluorophenyl)phenylmethyl]-1H-imidazole (I) or UR-4056, which is the subject of this invention, exhibited a very good activity against some species, together with good tolerance ($DL_{50}$=691 mg/kg in mice), good liposolubility (log P=3.09 in octanol-water) and appropiate pharmacokinetics.

The surprisingly good antifungal activity of UR-4056 can be better appreciated when it is compared with that of bifonazole, a recent well-developed commercial antifungal compound. Examples 18 to 20 show some comparative tests in which UR-4056 appears to be more potent than bifonazole in many instances.

Therefore, the invention is also directed to a pharmaceutical composition for treating fungal infections in humans and animals which comprises an antifungal effective amount of 1-[(2-fluorophenyl) (4-fluorophenyl)phenylmethyl]-1-H-imidazole or a pharmaceutically acceptable salt thereof, in combination with a pharmaceutically acceptable inert excipient.

Suitable pharmaceutically acceptable salts of 1-[(2-fluorophenyl) (4-fluorophenyl)phenylmethyl]-1H-imidazole are those obtained from physiologically tolerated inorganic and organic acids, such as sulfuric acid, hydrogen halide acids (hdyrochloric, hydrobromic . . . , sulphonic acids (methanesulphonic, p-toluenesulphonic . . . ), phosphoric acid, mono-, di- and trihydroxycarboxylic acids (acetic, maleic, fumaric, tartaric, lactic, salicylic, citric, ascorbic . . . ), etc.

By pharmaceutically acceptable, inert excipients there are to be understood solid, semi-solid or liquid diluents, fillers and formulation auxiliaries of all kinds. Tablets, pills, capsules, granules, solutions, suspensions, emulsions, suppositories, pastes, ointments, gels creams, lotions, powders and sprays containing 1-[(2-fluorophenyl)(4-fluorophenyl)phenylmethyl]-1H-imidazole may be mentioned as possible pharmaceutical preparations.

Accordingly the invention is further directed to the use of 1-[(2-fluorophenyl)(4-fluorophenyl)phenylmethyl]-1H-imidazole or a pharmaceutically acceptable salt thereof in preparation of a medicament for treating fungal infections in humans or animals.

The compound of the present invention mixed with pharmaceutically acceptable carriers can be administered by the oral route to humans and animals in the form of tablets, capsules, coated tablets, syrups, solutions, powder, etc., by injectable route, by rectal route, and by vaginal-intrauterine route in the form of an ovulum, vaginal tablet, ointment, cream, pessary, lotion, etc., at daily doses of from about 8 to 500, preferably 30 to 250 mg/kg of body weight; and by topical route in the form of a cream, lotion, ointment, emulsion, solution, shampoo, powder, gel, etc at concentrations ranging from 0.1 to 5%. However, is might be necessary to deviate from these dosage ranges and in particular to do so as a function of the condition and body weight of the patient being treated, the nature and severity of the illness, the nature of the composition, the route of administration, and the time or interval of the administration. In some cases, less than the above-mentioned amount is satisfactory, while in other cases the upper limit must be exceeded. The particular dosage which is optimum and the method of administration should, of course, be determined by a professional on the basis of the expert knowledge. Example 21 shows the composition of the most preferred pharmaceutical forms.

According to the present invention, the compounds of formula III, and in particular, 1-[(2-fluorophenyl) (4-fluorophenyl)phenylmethyl]-1H-imidazole, can be obtained in three steps according to the following scheme.

1) Carbinol Formation a) Method A

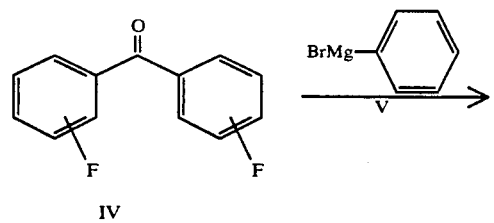

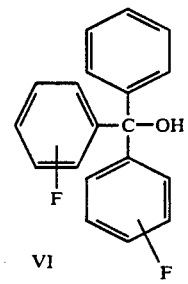

b) Method B

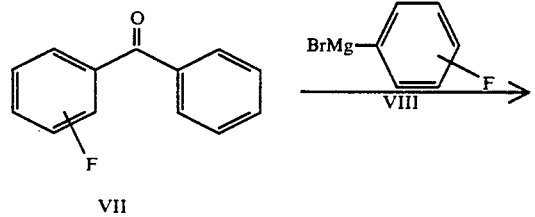

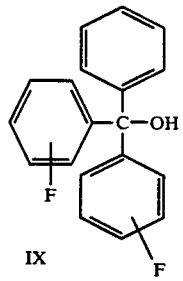

2) Formation of the Chloride

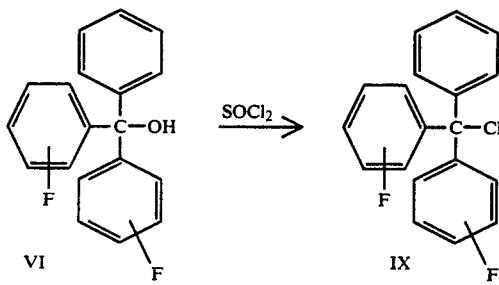

3) Preparation of the Final Product

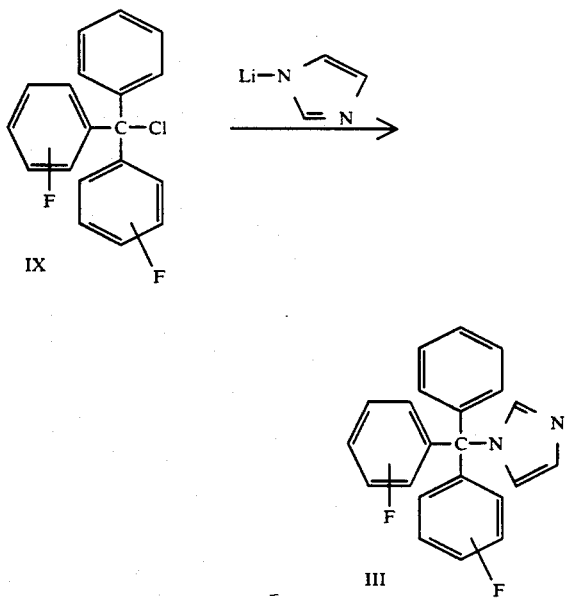

According to the method A of the first step, the difluorobenzophenone IV is reacted with phenylmagnesium bromide (V) to afford carbinol VI. Said reaction can be carried out at a temperature between 0° C. and that of the refluxing mixture, in an ethereal solvent, such as diethyl ether, or in a mixture of an ethereal solvent and a hydrocarbon, such as benzene or toluene. The unreacted starting materials can be separated by distillation of a water slurry (100° C.), and the resulting carbinol may be used in the next step without further purification.

Alternatively, carbinol VI can be obtained according to method B, that is, using a monofluoro benzophenone (VII) and fluorophenylmagnesium bromide (VIII). Although the yields of this method are slightly inferior, it represents a great advantage when the starting difluorobenzophenone is not commercially available or is difficult to prepare. The experimental conditions of this method are identical to those described in method A.

In a second step, carbinol VI is heated with thionyl chloride in the presence (or not) of a solvent to give the correspondent chloride IX. This compound can be isolated and characterized, or it can be used in the next step as obtained.

In the last step, intermediate IX is reacted with the lithium salt of imidazole, in a polar solvent, such as acetonitrile, at a temperature between 0° C. and 40° C., to afford the final product III. The reaction is instantaneous and need not to be heated. According to the State of the Art (*Arzneim. Forsch.*, 1972, 22, 1260), imidazole itself reacts with structurally similar chlorides, but it requires heat and longer periods of time. The method hereby described offers, thus, a cleaner and faster way of making the compounds of formula III. Lithium imidazolate is conveniently prepared by reaction of imidazole with a lithium base, such as n-butyllithium or lithium hydroxide.

The following examples further illustrate the invention:

EXAMPLE 1

[(2-Flurophenyl) (3-fluorophenyl)phenyl]carbinol

An oven-dried, 1-l flask was charged with magnesium turnings (2.91 g, 0.12 mol) and anhydrous ether (50 ml). A solution containing 1-bromo-2-fluorobenzene (20.12 g, 0.115 mol) in anhydrous ether (50 ml) was then added slowly, with vigorous stirring, at a rate that allowed a gentle reflux of the mixture. After the addition was finished, the reaction mixture was stirred at the refluxing temperature for 1 h and then cooled to 5°-10° C. A solution containing 2-fluorobenzophenone (20.0 g, 0.1 mol) in dry benzene (50 ml) was then added and the mixture heated to reflux for 6 h. The reaction was cooled to room temperature and carefully added to a mixture of ice and 1N aqueous hydrochloric acid. After stirring for 30 m, the organic layer was separated, washed with 10% aqueous sodium bicarbonate and then with water. The solvents were then removed on a rotatory evaporator. Water was added and the mixture was heated to 100° C. to distil water containing unreacted starting materials (15 h). The mixture was cooled to room temperature and water was decanted. The resulting white solid, pure by TLC analysis, was dried over phosphorus pentoxide, and used in the next step without further purification. For analytical pourposes, a sample was recrystallized from ether-petroleum ether to afford a white, crystalline solid.

mp: 108°-110° C.; IR (KBr) $\nu$: 3584, 3470, 3059, 1609, 1585, 1481, 1445, 1434, 1348, 1270, 755, 699 cm$^{-1}$.

Elemental analysis calculated for $C_{19}H_{14}F_2O$: C 77.01%; H 4.76%; F 12.82%. Found: C 77.00%; H 4.90%; F 12.40%.

EXAMPLE 2

[(2-Fluorophenyl) (4-fluorophenyl)phenyl]carbinol

Following the procedure described in example 1, but reacting phenylmagnesium bromide with 2,4'-difluorobenzophenone, the title compound was obtained in 97% yield. An analytical sample was obtained by recrystallization.

mp: 86.4°-86.8° C.; IR (KBr) $\nu$: 3591, 3465, 3077, 1597, 1575, 1502, 1481, 1445, 1337, 1269, 1224, 836, 759 cm$^{-1}$.

Elemental analysis calculated for $C_{19}H_{14}F_2O$: C 77.01%; H 4.76%; F 12.82%. Found: C 77.22%; H 4.28%; F 12.70%.

EXAMPLE 3

[Bis(3-fluorophenyl)phenyl]carbinol

Following the procedure described in example 1, but reacting 3-fluorophenylmagnesium bromide with 3-fluorobenzophenone, the title compound was obtained in 97% yield. An analytical sample was obtained by recrystallization.

mp: 114°-116° C.; IR (KBr) $\nu$: 3572, 3459, 3061, 1585, 1481, 1435, 1232, 786, 755, 699 cm$^{-1}$.

Elemental analysis calculated for $C_{19}H_{14}F_2O$: C 77.01%; H 4.76%; F 12.82%. Found: C 76.97%; H 5.25%; F 12.51%.

EXAMPLE 4

[(3-Fluorophenyl)(4-fluorophenyl)phenyl]carbinol

Following the procedure described in example 1, but using 4-fluorophenylmagnesium bromide and 3-fluorobenzophenone, the title compound was obtained in 90% yield. An analytical sample was prepared by recrystallization.

mp: 85°–92° C.; IR (KBr) $\nu$: 3580, 3445, 3057, 1607, 1597, 1585, 1500, 1479, 1435, 1230, 821, 699 cm$^{-1}$.

Elemental analysis calculated for $C_{19}H_{14}F_2O$: C 77.01%; H 4.76%; F 12.82%. Found: C 77.11%; H 5.01%; F 12.63%.

EXAMPLE 5

[Bis(4-fluorophenyl)phenyl]carbinol

Following the procedure described in example 1, but using phenylmagnesium bromide and 4,4'-difluorobenzophenone, the title compound was obtained in 84% yield. An analytical sample was prepared by recrystallization.

mp: 90°–93° C.; IR (KBr) $\nu$: 3469, 3058, 1599, 1503, 1234, 1158, 1010, 832, 699 cm$^{-1}$.

Elemental analysis calculated for $C_{19}H_{14}F_2O$: C 77.01%; H 4.76%; F 12.82%. Found: C 77.11%; H 5.01%; F 12.63%.

EXAMPLE 6

[(2-Fluorophenyl)(3-fluorophenyl)phenyl]chloromethane

To a cooled (0° C.) flask containing [(2-fluorophenyl)(3-fluorophenyl)phenyl]carbinol (20 g, 67.5 mmol) (obtained in example 1) was slowly added thionyl chloride (12.82 g, 108 mmol) with vigorous stirring. Once the reaction had been initiated (gas evolution), the rest of the thionyl chloride was added at once and the reaction mixture heated to reflux for 4 h. Volatiles were removed in vacuo and the remaining traces of thionyl chloride were removed by azeotropic evaporation with toluene (2×). The resulting residue was dissolved in petroleum ether and precipitated by cooling to −20° C. The solid was filtered and dried to afford the title compound as a slightly cream-colored solid (18.1 g, 85%).

mp: 69.2°–71.6° C.; IR (KBr) 3110, 1638, 1618, 1512, 1475, 1300, 1258, 788, 770 cm$^{-1}$.

Elemental analysis calculated for $C_{19}H_{13}ClF_2$: C 72.50%; H 4.16%; Cl 11.26%; F 12.07%. Found: C 72.62%; H 4.04%; Cl 11.42%; F 11.90%.

EXAMPLE 7

[(2-Fluorophenyl)(4-fluorophenyl)phenyl]chloromethane

Following the procedure described in the previous example, but using the carbinol obtained in example 2, the title compound was obtained in 83% yield.

mp: 65.2°–65.7° C.; IR (KBr) $\nu$: 3054, 1603, 1574, 1502, 1480, 1442, 1228, 1162, 838, 759 cm$^{-1}$.

Elemental analysis calculated for $C_{19}H_{13}ClF_2$: C 72.50%; H 4.16%; Cl 11.26%; F 12.07%. Found: C 72.73%; H 4.36%; Cl 10.86%; F 11.98%.

EXAMPLE 8

[Bis(3-fluorophenyl)phenyl]chloromethane

Following the procedure described in example 6, but using the carbinol obtained in example 3, the title compound was obtained in 93% yield.

mp: 70°–73° C.; IR (KBr) $\nu$: 3080, 1621, 1598, 1495, 1450, 1250, 780, 750 cm$^{-1}$.

Elemental analysis calculated for $C_{19}H_{13}ClF_2$: C 72.50%; H 4.16%; Cl 11.26%; F 12.07%. Found: C 71.95%; H 4.26%; Cl 11.24%; F 11.83%.

EXAMPLE 9

[(3-Fluorophenyl)(4-fluorophenyl)phenyl]chloromethane

Following the procedure described in example 6, but using the carbinol obtained in example 4, the title compound was obtained in 80% yield.

mp: 59.8°–61.8° C.; IR (KBr) $\nu$: 3061, 1606, 1587, 1503, 1482, 1443, 1435, 1236, 1162, 780, 744, 697 cm$^{-1}$.

Elemental analysis calculated for $C_{19}H_{13}ClF_2$: C 72.50%; H 4.16%; Cl 11.26%; F 12.07%. Found: C 71.41%; H 3.96%; Cl 10.59%; F 11.96%.

EXAMPLE 10

[Bis(4-fluorophenyl)phenyl]chloromethane

Following the procedure described in example 6, but using the carbinol obtained in example 5, the title compound was obtained in 71% yield.

mp: 45°–47° C.; IR (KBr) $\nu$: 3080, 1660, 1610, 1515, 1235, 845, 570 cm$^{-1}$.

Elemental analysis calculated for $C_{19}H_{13}ClF_2$: C 72.50%; H 4.16%; Cl 11.26%; F 12.07%. Found: C 72.52%; H 4.46%; Cl 10.76%; F 12.41%.

EXAMPLE 11

Lithium imidazolate a) From imidazole and n-butillithium

To a cold (−60° C.) solution of imidazole (1.56 g, 22.9 mmol) in dry tetrahydrofuran (100 ml) was added a 1.6M solution of n-butyllithium in hexane (14 ml, 22.9 mmol). The mixture was warmed slowly to room temperature, resulting in the formation of a white precipitate. The slurry was stirred for 1.5 h, then cooled to 0° C. and filtered. The resulting white solid was dried under vacuum ($P_2O_5$, 50° C., 18 h) to afford 1.66 g (98%) of product. This material is hygroscopic and must be kept in a dessicator for storage. Nevertheless, the yield of the following reaction seems to be unaffected by the presence of humidity.

IR (KBr) $\nu$: 3417, 3121, 3017, 2914, 2823, 2793, 2697, 2614, 2539, 1495, 1429, 1326, 1262, 1055, 936 cm$^{-1}$.

b) From imidazole and lithium hydroxide

A solution containing imidazole (6.8 g, 0.1 mol) and lithium hydroxide monohydrate (4.19 g, 0.1 mol) in water (50 ml) was stripped down on a rotary evaporator. Ethanol was added and the mixture was concentrated again (2×) in order to remove residual water. The resulting white solid was dried under vacuum (50° C., $P_2O_5$, 12 h) to afford 7.83 g of product containing variable amounts of water. As in the previous case, the presence of water in this compound does not affect the yield of the next step.

EXAMPLE 12

1-[(2-Fluorophenyl)(3-fluorophenyl)phenylmethyl]-1H-imidazole (UR-4055).

To a solution of [(2-fluorophenyl)(3-fluorophenyl)phenyl]chloromethane (5 g, 16.87 mmol), (obtained in example 6) in acetonitrile (15 ml), was added lithium imidazolate (1.37 g, 18.5 mmol), resulting in a slight increase of the temperature (40° C.). The mixture was stirred at room temperature for 2 h, then added to cold water. The resulting solid was filtered, washed with water until neutral pH, and dried to afford the product (5.61 g, 96%) as a white solid. TLC analysis revealed presence of a trace of carbinol, possibly already present in the chloride. An analytical sample was obtained by recrystallization from acetonitrile.

mp: 145°–148° C.; IR (KBr) ν: 3429, 3064, 1609, 1587, 1482, 1445, 1276, 1230, 1209, 1072, 752 cm$^{-1}$.

Elemental analysis calculated for $C_{22}H_{16}F_2N_2$: C 76.28%; H 4.66%; N 8.08%; F 10.97%. Found: C 76.56%; H 4.69%; N 7.98%; F 10.35%.

EXAMPLE 13

1-[(2-Fluorophenyl)(4-fluorophenyl)phenylmethyl]-1H-imidazole (UR-4056)

Following the procedure described in example 12, but using [(2-fluorophenyl)(4-fluorophenyl)]phenyl chloromethane (obtained in example 7) the title product was obtained in 99% yield. Recrystallization from acetonitrile gave an analytical sample.

mp: 164°–167° C.; IR (KBr) ν: 3118, 1601, 1574, 1504, 1481, 1443, 1225, 1165, 1075, 831, 819, 758 cm$^{-1}$.

Elemental analysis calculated for $C_{22}H_{16}F_2N_2$: C 76.28%; H 4.66%; N 8.08%; F 10.97%. Found: C 76.06%; H 4.63%; N 8.02%; F 10.92%.

EXAMPLE 14

1-[Bis(3-fluorophenyl)phenylmethyl]-1H-imidazole (UR-4057)

Following the procedure described in example 12, but using [bis(3-fluorophenyl)phenyl]chloromethane (obtained in example 8) the title product was obtained in 94% yield. Recrystallization from acetonitrile afforded an analytical sample.

mp: 165°–167° C.; IR (KBr) ν: 3067, 1607, 1586, 1480, 1431, 1273, 1229, 1209, 1073, 786, 750, 699 cm$^{-1}$.

Elemental analysis calculated for $C_{22}H_{16}F_2N_2$: C 76.28%; H 4.66%; N 8.08%; F 10.97%. Found: C 76.84%; H 4.81%; N 8.09%; F 10.71%.

EXAMPLE 15

1-[(3-Fluorophenyl)(4-fluorophenyl)phenylmethyl]-1H-imidazole (UR-4058).

Following the procedure described in example 12, but using [(3-fluorophenyl)(4-fluorophenyl)phenyl]-chloromethane (obtained in example 9) the title compound was obtained in 100% yield. An analytical sample was prepared by recrystallization from acetonitrile.

mp: 138°–141° C.; IR (KBr) ν: 3063, 1610, 1600, 1586, 1500, 1480, 1441, 1233, 1207, 1161, 1070, 900, 815, 752, 697 cm$^{-1}$.

Elemental analysis calculated for $C_{22}H_{16}F_2N_2$: C 76.28%; H 4.66%; N 8.08%; F 10.97%. Found: C 76.56%; H 4.92%; N 7.99%; F 10.81%.

EXAMPLE 16

1-[Bis(4-fluorophenyl)phenylmethyl]-1H-imidazole (UR-4059)

Following the procedure described in example 12, but using [bis(4-fluorophenyl)phenyl]chloromethane (obtained in example 10), the title compound was obtained in 92% yield. An analytical sample was prepared by recrystallization from acetonitrile.

mp: 135°–138° C.; IR (KBr) ν: 3106, 3056, 3042, 1599, 1505, 1239, 1229, 1214, 1168, 1109, 1076, 824, 747, 703 cm$^{-1}$.

Elemental analysis calculated for $C_{22}H_{16}F_2N_2$: C 76.28%; H 4.66%; N 8.08%; F 10.97%. Found: C 76.28%; H 4.67%; N 7.89%; F 10.21%.

EXAMPLE 17

1-[(2-Fluorophenyl)(4-fluorophenyl)phenylmethyl]-1H-imidazole (UR-4056).

Following the procedure described in example 13 but using 1H-imidazole in place of lithium imidazolate, the title compound is obtained in 71% yield after flash chromatography purification. Analytical data as in example 13.

EXAMPLE 18

The antifungal activity of 1-[(2-fluorophenyl)(4-fluorophenyl)phenylmethyl]-1H-imidazole was shown by its ability to inhibit the growth of different species of yeast and filamentous fungi in vitro. The activity was recorded as the MIC value, that is, the minimum amount of product needed to achieve the complete inhibition of the in vitro growth of the test organism. Testing was performed as follows: a solution of the antifungal agent in ethanol was diluted with DST agar (pH 6.5) or Emmon's Sabouraud dextrose agar to obtain concentrations between 10 and 0.01 mcg/ml, or 80 and 0.16 mcg/m, respectively. The inoculum was standarized in order $1 \times 10^5$ cfu/ml, and 10 mcl of each organism was seeded into the agar surface. Incubation was then allowed at 30° C. during 3 days (DST) or 2 days (Emmon's) for yeasts and 10 days for filamentous fungi. Following incubation, the zones of inhibition were measured and compared to an inoculated, drug-free control to yield the MIC value.

The following table shows the MIC values of UR-4056 and bifonazole for different organisms in 10 DST and Emmon's media.

| | MIC (mcg/ml) | | | |
|---|---|---|---|---|
| | DST agar | | Emmon's Sabouraud dextrose agar | |
| | UR-4056 | Bifonazole | UR-4056 | Bifonazole |
| C. albicans ATCC 10231 | 1.00 | 1.00 | 0.04 | 0.63 |
| C. albicans ATCC 28516 | 0.50 | 2.50 | 0.04 | 0.63 |
| C. guilliermondii SQ 2210 | 1.00 | 10.00 | 0.16 | 5.00 |
| C. tropicalis SQ 1647 | 1.00 | 10.00 | 0.63 | 10.00 |
| C. guilliermondii (clinica) | 5.00 | 10.00 | 5.00 | 40.00 |
| C. albicans serotipo B | 0.50 | 10.00 | 0.31 | 20.00 |
| C. albicans serotipo A | 1.00 | 2.50 | 1.25 | 2.50 |
| S. cerevisiae ATCC 9763 | 0.10 | 0.25 | 0.31 | 0.63 |
| C. pseudotropicalis ATCC 28838 | 0.025 | 0.05 | 0.63 | 1.25 |
| Rhodotorula rubra | 0.10 | 0.05 | 0.08 | 0.04 |
| C. parapsilosis (clinica) | 0.50 | 10.00 | 0.08 | 20.00 |
| T. glabrata (clinica) | 0.05 | 0.05 | 0.31 | 0.16 |
| T. mentagrophytes ATCC 9972 | 0.25 | 1.00 | 1.25 | 5.00 |
| T. mentagrophytes ATCC 9129 | 0.05 | 2.50 | 0.31 | 2.50 |
| Aspergillus niger | 0.25 | 0.10 | 2.50 | 2.50 |
| Aspergillus flavus | 1.00 | 10.00 | 2.50 | 80.00 |
| Aspergillus fumigatus (1) | 0.50 | 0.10 | 0.63 | 0.31 |
| Aspergillus | 0.50 | 1.00 | 1.25 | 1.25 |

-continued

| | MIC (mcg/ml) | | | |
|---|---|---|---|---|
| | DST agar | | Emmon's Sabouraud dextrose agar | |
| | UR-4056 | Bifonazole | UR-4056 | Bifonazole |
| *fumigatus* (2) | | | | |
| *Microsporum gypseum* | 0.50 | 0.10 | 1.25 | 0.63 |
| *Microsporum gypseum* (-) | 0.10 | 2.50 | 0.63 | 5.00 |
| *Microsporum audouini* ATCC 9079 | 0.05 | 0.05 | 0.63 | 5.00 |
| *Microsporum canis* (clinica) | 0.025 | 0.025 | 0.63 | 2.50 |
| *T. mentagrophytes* (clinica) (1) | 0.10 | 0.50 | 1.25 | 5.00 |
| *T. mentagrophytes* (clinica) (2) | 10.000 | 10.000 | 40.00 | 80.00 |
| *T. mentagrophytes* (clinica) (3) | 0.25 | 1.00 | 0.16 | 5.00 |
| *T. mentagrophytes* (clinica) (4) | 0.10 | 0.50 | 1.25 | 5.00 |
| *T. mentagrophytes* (clinica) (5) | 0.10 | 1.00 | 1.25 | 5.00 |

EXAMPLE 19

The growth inhibition percentage of 5 different isolates on shake cultures was determined 24 h and 48 h after incubation at 28° C. Testing was performed as follows: a solution of the antifungal agent in ethanol was diluted with Kimming's broth (pH 7) to obtain concentrations between 8 and 0.062 mcg/ml. Inoculum size was $10^3$ cfu/ml. The growth inhibition percentage was determined by spectrophotometry (450 nm). The results obtained for 1-[(2-fluorophenyl)(4-fluorophenyl)-phenylmethyl]-1H-imidazole and bifonazole are shown in the following 5 tables.

| Antifungal concentration (mcg/ml) | GROWTH (%) | | | |
|---|---|---|---|---|
| | 24 h | | 48 h | |
| | UR-4056 | Bifonazole | UR-4056 | Bifonazole |
| *C. parapsilosis* | | | | |
| 0.062 | 0.40 | 99.85 | 2.42 | 100.00 |
| 0.125 | 0.60 | 80.14 | 0.72 | 100.00 |
| 0.25 | 0.20 | 61.05 | 0.68 | 93.82 |
| 0.5 | 0.20 | 39.85 | 0.50 | 78.23 |
| 1 | 0.33 | 25.59 | 0.28 | 68.09 |
| 2 | 0.06 | 16.01 | 0.24 | 37.14 |
| 4 | 0.27 | 9.02 | 0.24 | 19.94 |
| 8 | 0.60 | 9.00 | 0.20 | 19.00 |

| Antifungal concentration (mcg/ml) | GROWTH (%) | | | |
|---|---|---|---|---|
| | 24 h | | 48 h | |
| | UR-4056 | Bifonazole | UR-4056 | Bifonazole |
| *C. guilliermondii* | | | | |
| 0.062 | 21.73 | 100.00 | 76.55 | 100.00 |
| 0.125 | 15.95 | 92.18 | 49.38 | 100.00 |
| 0.25 | 7.96 | 62.32 | 23.05 | 96.67 |
| 0.5 | 2.82 | 39.79 | 15.46 | 88.59 |
| 1 | 1.03 | 29.89 | 6.66 | 85.90 |
| 2 | 0.00 | 12.82 | 1.84 | 40.32 |
| 4 | 0.00 | 7.57 | 0.08 | 20.03 |
| 8 | 0.00 | 7.40 | 0.06 | 18.84 |
| *C. albicans* ATCC 10231 | | | | |
| 0.062 | 37.43 | 98.73 | 75.41 | 99.14 |
| 0.125 | 26.01 | 97.85 | 67.19 | 99.12 |
| 0.25 | 23.46 | 83.55 | 59.01 | 94.25 |
| 0.5 | 21.03 | 46.15 | 57.00 | 78.31 |
| 1 | 14.41 | 23.32 | 44.33 | 49.26 |
| 2 | 5.42 | 4.74 | 27.55 | 19.66 |
| 4 | 1.84 | 2.68 | 12.38 | 16.82 |
| 8 | 1.15 | 2.13 | 12.79 | 12.73 |
| *C. tropicalis* | | | | |
| 0.062 | 10.29 | 96.28 | 17.91 | 100.00 |
| 0.125 | 3.51 | 94.11 | 12.55 | 100.00 |
| 0.25 | 2.61 | 85.52 | 12.49 | 95.30 |
| 0.5 | 2.10 | 62.73 | 4.43 | 79.50 |
| 1 | 1.52 | 49.02 | 3.97 | 75.00 |
| 2 | 0.43 | 10.85 | 0.77 | 69.02 |
| 4 | 0.45 | 3.07 | 0.09 | 17.33 |
| 8 | 0.38 | 1.82 | 0.00 | 6.00 |
| *T. glabrata* | | | | |
| 0.062 | 69.09 | 5.69 | 99.39 | 92.36 |
| 0.125 | 28.05 | 2.85 | 99.39 | 83.29 |
| 0.25 | 15.58 | 2.08 | 99.00 | 21.23 |
| 0.5 | 10.05 | 1.79 | 99.00 | 6.15 |
| 1 | 3.34 | 1.08 | 94.37 | 4.20 |
| 2 | 2.83 | 0.68 | 19.82 | 2.28 |
| 4 | 1.16 | 0.42 | 14.85 | 3.93 |
| 8 | 0.32 | 0.60 | 4.12 | 3.00 |

EXAMPLE 20

The antifungal activity of 1-[(2-fluorophenyl)(4-fluorophenyl)phenylmethyl]-1H-imidazole and bifonazole was determined by serial dilutions in Sabouraud gentamycin broth using microplates. The antifungal agent was diluted in 50% ethanol to obtain concentrations between 40 and 0.015 mcg/ml. Inoculum was $10^7$ cfu/ml for yeast and $10^6$ cfu/ml for dermatophytes. Incubation was allowed at 37° C. during 2 days for yeasts, and at 29° C. during 7 days for dermatophytes. MIC's were determined as in example 18. The MIC distributions obtained in 9 organisms are shown in the next tables.

TABLE 1

| | MIC Distribution (*C. albicans* # of strains = 50) | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | 5 | 31 | 11 | 2 | — | 1 | — | — | — | — |
| BIFONAZOLE | 4 | — | 1 | 11 | 28 | 6 | — | — | — | — | — | — | — |

TABLE 2

| | MIC Distribution (*C. tropicalis* # of strains = 30) | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | 8 | 13 | 4 | 3 | 1 | — | — | 1 | — | — |
| BIFONAZOLE | 27 | — | — | 1 | 2 | — | — | — | — | — | — | — | — |

TABLE 3

| MIC Distribution (*C. parapsilosis* # of strains 10 = UR-4056/14 = Bifonazole) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | 2 | — | — | 1 | 2 | 2 | 1 | — | — | 2 |
| BIFONAZOLE | 10 | — | — | 2 | 1 | — | — | 1 | — | — | — | — | — |

TABLE 4

| MIC Distribution (*C. guilliermondii* # of strains = 5) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | — | — | — | 2 | 2 | 1 | — | — | — | — |
| BIFONAZOLE | 5 | — | — | — | — | — | — | — | — | — | — | — | — |

TABLE 5

| MIC Distribution (*C. krusei* # of strains = 5) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | 1 | — | — | — | — | 2 | 1 | — | 1 | — | — | — | — |
| BIFONAZOLE | 3 | — | — | 1 | — | 1 | — | — | — | — | — | — | — |

TABLE 6

| MIC Distribution (*T. glabrata* # of strains = 10 = UR-4056/15 Bifonzaole) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | 1 | — | 1 | 4 | 2 | 1 | — | 1 | — | — | — | — | — |
| BIFONAZOLE | 2 | — | — | 3 | 5 | 3 | — | 1 | — | 1 | — | — | — |

TABLE 7

| MIC Distribution (*T. mentagrohytes* # of strains = 17) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | — | — | — | 3 | 11 | 2 | 1 | — | — | — |
| BIFONAZOLE | — | — | — | — | — | 5 | 10 | 1 | — | — | — | — | 1 |

TABLE 8

| MIC Distribution (*M. canis* # of strains = 13) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | — | — | — | 4 | 5 | — | 4 | — | — | — |
| BIFONAZOLE | — | — | — | — | — | 5 | 4 | 2 | — | — | — | 1 | — | 1 |

TABLE 9

| MIC Distribution (*T. rubrum* # of strains = 6) | | | | | | | | | | | | | |
|---|---|---|---|---|---|---|---|---|---|---|---|---|---|
| ANTIFUNGAL | 40 | 40 | 20 | 10 | 5.0 | 2.5 | 1.2 | 0.6 | 0.3 | 0.15 | 0.078 | 0.038 | 0.038 |
| UR-4056 | — | — | — | — | — | 1 | 1 | — | — | 4 | — | — | — |
| BIFONAZOLE | — | — | — | — | 1 | — | 1 | 1 | 1 | — | — | — | 2 |

EXAMPLE 21

1. Gynecological Tablet

| | |
|---|---|
| UR-4056 | 500 mg |
| Citric acid | 140 mg |
| Sodium citrate | 195 mg |
| Lactose | 314 mg |
| Microcrystalline cellulose | 240 mg |
| Polyethylene glycol sorbitanoleate | 4 mg |
| Magnesium stearate | 35 mg |
| Crosslinked polyvinylpyrrolidinone | 85 mg |

2. Gynecological Cream

| | |
|---|---|
| UR-4056 | 2.00 g |
| Sorbitan fatty acid ester | 2.00 g |
| Polyoxyethylene sorbitan fatty acid ester | 1.50 g |
| Artificial spermacety | 3.00 g |
| Cetyl stearyl alcohol | 3.50 g |
| Isopropyl myristate | 13.50 g |
| Banzyl alcohol | 1.00 g |
| Monosodium citrate | 0.03 g |
| Purified water | 73.47 g |

3. Dermic Cream

| | |
|---|---|
| UR-4056 | 1.0 g |
| Dimethyl acetamide | 2.0 g |
| White petrolatum | 25.0 g |
| Stearyl alcohol | 22.0 g |
| Propylene glycol | 12.0 g |
| Sodium lauryl sulfate | 1.5 g |
| Methylparaben | 0.3 g |

-continued

| | |
|---|---|
| Purified water | 32.6 g |

4. Dermic Spray

| | |
|---|---|
| UR-4056 | 1 g |
| Benzyl alcohol | 5 g |
| Hydroxypropyl cellulose | 10 g |
| Isopropanol | 44 g |
| Propellant agent 12/114 (40:60) | 40 g |

We claim:

1. -1-[(2-Fluorophenyl)(4-fluorophenyl)phenylmethyl]-1H-imidazole or a pharmaceutically acceptable salt thereof.

2. -A pharmaceutical composition for treating fungal infections in humans or animals which comprises an antifungal effective amount of 1-[(2-fluorophenyl) (4-fluorophenyl)phenylmethyl]-1H-imidazole or a pharmaceutically acceptable salt thereof, in combination with a pharmaceutically acceptable inert excipient.

3. -Method for treating antifungal infections in humans or animals which comprises administering to a human or animal an antifungal effective dose of 1-[(2-fluorophenyl)(4-fluorophenyl)phenylmethyl]-1H-imidazole or a pharmaceutically acceptable salt thereof in combination with a pharmaceutically acceptable inert excipient.

* * * * *